US010967076B2

(12) United States Patent
Van Zijl et al.

(10) Patent No.: US 10,967,076 B2
(45) Date of Patent: Apr. 6, 2021

(54) USE OF NON-LABELED SUGARS AND DETECTION BY MRI FOR ASSESSING TISSUE PERFUSION AND METABOLISM

(71) Applicant: The Johns Hopkins University, Baltimore, MD (US)

(72) Inventors: Peter C. Van Zijl, Baltimore, MD (US); Dmitri Artemov, Baltimore, MD (US); Kannie Wai Yan Chan, Baltimore, MD (US); Yoshinori Kato, Baltimore, MD (US); Michael T. McMahon, Baltimore, MD (US); Guanshu Liu, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/877,754

(22) Filed: Oct. 7, 2015

(65) Prior Publication Data

US 2016/0095945 A1 Apr. 7, 2016

Related U.S. Application Data

(62) Division of application No. 13/994,600, filed as application No. PCT/US2011/064868 on Dec. 14, 2011, now Pat. No. 9,180,211.

(60) Provisional application No. 61/422,911, filed on Dec. 14, 2010.

(51) Int. Cl.
| | |
|---|---|
| *A61K 49/10* | (2006.01) |
| *A61B 5/055* | (2006.01) |
| *A61B 5/145* | (2006.01) |
| *G01R 33/56* | (2006.01) |
| *A61B 5/026* | (2006.01) |
| *A61B 5/00* | (2006.01) |
| *A61M 5/142* | (2006.01) |

(52) U.S. Cl.
CPC .............. *A61K 49/10* (2013.01); *A61B 5/026* (2013.01); *A61B 5/055* (2013.01); *A61B 5/14532* (2013.01); *A61B 5/14539* (2013.01); *A61B 5/4866* (2013.01); *A61B 5/74* (2013.01); *A61M 5/142* (2013.01); *G01R 33/5605* (2013.01)

(58) Field of Classification Search
CPC .......... A61B 5/00; A61B 5/5026; A61K 49/10
See application file for complete search history.

(56) References Cited

U.S. PATENT DOCUMENTS

| | | |
|---|---|---|
| 6,963,769 B1 | 11/2005 | Balaban et al. |
| 6,994,841 B1 | 2/2006 | Rocklage et al. |
| 7,498,018 B2 | 3/2009 | Williams, III |
| 7,683,617 B2 | 3/2010 | Van Zijl et al. |
| 2003/0211036 A1* | 11/2003 | Degani ............... A61B 5/0263 424/1.11 |
| 2008/0167549 A1* | 7/2008 | Balaban .............. A61B 5/055 600/420 |
| 2008/0197840 A1* | 8/2008 | Van Zijl .............. G01R 33/485 324/307 |

OTHER PUBLICATIONS

Muhammad Haque et al., Functional MRI of Liver Using BOLD MRI:Effect of Glucose, Journal of Magnetic Resonance Imaging, 2010, 32, 988-991.*
Jimin Ren et al. Imaging the Tissue Distribution of Glucose in Livers Using a PARACEST Sensor, Magn Reson Med. 60(5), 1047-1055. (Year: 2008).*
Muhammad Haque et al. Functional MRI of Liver Using Bold MRI: Effect of Glucose, Journal of Magnetic Resonance Imaing, 32, 988-991. (Year: 2010).*
Tao Jin et al. Mapping brain glucose uptake with chemical exchange-sensitive spin-lock magnetic resonance imaging, Journal of Cerebral Blood Flow & Metabolism, 34, 1402-1410. (Year: 2014).*
David L Thomas et al. The measurement of diffusion and perfusion in biological systems using magnetic resonance imaging, Phys. Med. Biol, 45, R97-R138. (Year: 2000).*
Yen-Wen Wu et al. Comparison of Contrast-Enhanced MRI with 18F-FDG PET/201TI SPECT in Dysfunctional Myocardium: Relation to Early Functional Outcome After Surgical Revascularization in Chronic Ischemic Heart Disease, J Nucl Med, 48, 1096-1103. (Year: 2007).*
Aime et al., Targeting cells with MR imaging probes based on paramagnetic Gd(III) chelates, *Curr Pharm Biotechnol* 5, 509-518, (2004).
Allege et al., Breast cancer models to study the expression of estrogen receptors with small animal PET imaging, *Nuci Med Biol* 31, 761-770, (2004).
Ardenkjaer-Larsen et al., Increase in signal-to-noise ratio of >10,000 times in liquid-state NMR. *Proceedings of the National Academy of Sciences of the USA* 100, 10158-10163, (2003).
Artemov et al., In vivo selective measurement of (1-13C)-glucose metabolism in tumors by heteronuclear cross polarization. *Magn Reson Med* 33, 151-155, (1996).
Artemov et al., Two-compartment model for determination of glycolytic rates of solid tumors by in vivo 13C NMR spectroscopy. *NMR Biomed* 11, 395-404, (1998).

(Continued)

*Primary Examiner* — Michael G. Hartley
*Assistant Examiner* — Jagadishwar R Samala
(74) *Attorney, Agent, or Firm* — Venable LLP; Henry J. Daley; Aziz H. Poonawalla

(57) ABSTRACT

A method for magnetic resonance (MR) imaging or spectroscopy on a MR scanner to detect tissue physiological parameters in one or more tissue areas in a human or non-human subject includes administering to the subject a contrast enhancing physiologically tolerable amount of a sugar that is non-labeled, subjecting the subject to an MR procedure capable of generating MR signals encoding at least one tissue area in the subject in which the sugar either passes or is taken up, detecting a temporal variation in the MR signals in the at least one tissue area after the administering the sugar, determining at least one tissue-related parameter from the temporal variation, and ascertaining whether the at least one tissue-related parameter is abnormal.

5 Claims, 14 Drawing Sheets

(56) References Cited

OTHER PUBLICATIONS

Atanasijevic et al., Calcium-sensitive MRI contrast agents based on superparamagnetic iron oxide nanoparticies and calmodulin. *Proceedings of the National Academy of Sciences of the United States of America* 103, 14707-14712, (2006).
Avril, N. & Adler, L, P, F-18 fluorodeoxyglucose-positron emission tomography Imaging for primary breast cancer and loco-regional staging. *Radial Clin North Am* 45, 645-657, vi, (2007).
Avril et al., Breast imaging with fluorine-18-FDG PET; quantitative image analysis, *J Nuci Med* 38, 1186-1191, (1997).
Blasberg et al., Molecular-genetic imaging: a nuclear medicine-based perspective. *Mo! Imaging* 1, 280-300, (2002).
Bluemke et al., Magnetic resonance Imaging of the breast prior to biopsy. JAMA 292, 2735-2742, (2004).
Bohndie et al., Imaging and 'amid methods for the molecular diagnosis of cancer. Expert Rev Mol Diagn 10, 417-434, (2010).
Bulte et al., Iron oxide MR contrast agents for molecular and cellular imaging, NMR Biomed 17, 484-499, (2004).
Caravan, P. Strategies for increasing the sensitivity of gadolinium based MRI contrast agents, Chem Soc Rev 35, 512-523, (2006).
Catana et al., Simultaneous in vivo positron emission tomography and magnetic resonance imaging. Proceedings of the National Academy of Sciences of the United States of America 105, 3705-3710, (2008).
Chan et al., "Imaging of glucose uptake in breast tumors using non-labeled D-glucose," Proc. Intl. Soc. Mag. Reson. Med. 19(2011), 551.
Contag et al., It's not just about anatomy: in vivo bioluminescence imaging as an eyepiece Into biology. *J Magn Reson Imaging* 16, 378-387, (2002).
Craciunescu et al., DCE-MRI parameters have potential to predict response of locally advanced breast cancer patients to neoadjuvant chemotherapy and hyperthermia: A pilot study. *Int J Hyperthermia*, 1-11, (2009).
de Graaf et al., In vivo 1H-[13q-NMR spectroscopy of cerebral metabolism. *NMR Biomed* 16, 339-357, (2003).
Degani et al., Nat. Med. 3, 780, 1997.
Escalona et al., A systematic review of FDG-PET in breast cancer. *Med Onoo/* 27, 114-129, (2010).
Esserman et al., Magnetic resonance imaging captures the biology of ductal carcinoma in situ. J Clin Oncol 24, 4603-4610, (2006).
Extended European Search Report issued in European Patent Application No. 11848032.6 dated Apr. 28, 2014.
Facey et al., Overview of the clinical effectiveness of positron emission tomography imaging in selected cancers. Health Technol Assess 11, iii-iv, x1-267, (2007).
Furman-Haran et al., Dynamic contrast-enhanced magnetic resonance imaging reveals stress-induced angiogenesis in MCF7 human breast tumors. Proceedings of the National Academy of Sciences of the United States of America 93, 6247-6251, (1996).
Gasparini, G. Prognostic value of vascular endothelial growth factor in breast cancer. Oncologist 5 Suppl 1, 37-44, (2000).
Gatenby et al., Why do cancers have high aerobic glycolysis7 Nat Rev Cancer 4, 891-899, (2004).
Gillies, R. J. In vivo molecular imaging. J Cell Biochem Suppl 39, 231-238, (2002).
Golman et al., Molecular imaging using hyperpolarized 13C, Br J Radiol 76 Spec No. 2, S118-127, (2003).
Golman et al., Metabolic Imaging by hyperpolarized 13C magnetic resonance Imaging for In vivo tumor diagnosis. Cancer Res 66, 10855-10860, (2006).
Gross et al., Spying on cancer: molecular imaging in vivo with genetically encoded reporters, Cancer Cell 7, 5-15, (2005).
Gruetter et al., Localized in vivo 13C NMR spectroscopy of the brain, NMR 8/Dazed 16, 313-338, (2003).
Gruetter et al., Non-invasive measurements of the cerebral steady-state glucose concentration and transport in humans by 13C nuclear magnetic resonance. Adv Exp Med Bid 331, 35-40, (1993).

Heudel et al., Value of PET-FDG in primary breast cancer based on histopathological and Immunohistochemical prognostic factors. Int J Clin Oncol, (2010).
Huang et al., The magnetic resonance shutter speed discriminates vascular properties of malignant and benign breast tumors in vivo. Proceedings of the National Academy of Sciences of the United States of America 106, 17943-17948, (2008).
Hwang et al., "Modulation of Murine Radiation-Induced Fibrosarcoma-1 Tumor Metabolism and Blood Flow in Situ Via Glucose and Mannitol Administration Monitored by 31P and 2H Nuclear Magnetic Resonance Spectroscopy," Cancer Research, vol. 51, No. 12, 1991, pp. 3108-3118.
Jacobs et al., Multiparametric and multinuclear magnetic resonance imaging of human breast cancer: current applications, *Technol Cancer Res Treat* 3, 543-550, (2004).
Josephson et al., High-efficiency intracellular magnetic labeling with novel superparamagnetic-Tat peptide conjugates. *Bioconjug Chem* 10, 186-191, (1999).
Kang et al., Clinical significance of glucose transporter 1 (GLUT1) expression in human breast carcinoma. *Jpn J Cancer Res* 93, 1123-1128, (2002).
Kauppinen et al., "Nuclear magnetic resonance spectroscopy studies of the brain," Progress in Neurobiology, vol. 44, No. 1, 1994, pp. 87-118.
Kim et al., Water saturation shift referencing (WASSR) for chemical exchange saturation transfer (GEST) experiments, Magn Reson Med 61, 1441-1450, (2009).
Knopp et al., MR mammography with pharmacokinetic mapping for monitoring of breast cancer treatment during neoadjuvant therapy. Magn Reson Imaging Clin N Am 2, 633-658, (1994).
Knopp et al., Functional magnetic resonance imaging in oncology for diagnosis and therapy monitoring, Mal Cancer Thor 2, 419-426, (2003).
Knopp et al., Pathophysiologic basis of contrast enhancement in breast tumors. J Magn Reson Imaging 10, 260.266, (1999).
Kumar et al., The role of 18F-FDG PET/CT in evaluation of early response to neoadjuvant chemotherapy in patients with locally advanced breast cancer. Eur Radiol 19, 1347-1357, (2009).
Kurhanewicz et al., Current and potential applications of clinical 13C MR spectroscopy. J Nucl Med 49, 341-344, (2008).
Li et al., Shutter-speed analysis of contrast reagent bolus-tracking data: Preliminary observations in benign and malignant breast disease. Magn Reson Med 53, 724-729, (2005).
Lyon et al., Glucose metabolism in drug-sensitive and drug-resistant human breast cancer cells monitored by magnetic resonance spectroscopy. Cancer Res 48, 870.877, (1988).
Mancuso et al., Real-time detection of 13C NMR labeling kinetics in perfused EMT6 mouse mammary tumor cells and betaHC9 mouse insulinomas. *Blotechnol Bloeng* 87, 835-848, (2004).
Mason et al., Rat brain glucose concentration and transport kinetics determined with 13C nuclear magnetic resonance spectroscopy. *Adv Exp Med Biol* 331, 29-34, (1993).
Massoud et al., Molecular imaging in living subjects: seeing fundamental biological processes in a new light. *Genes Dev* 17, 545-580, (2003).
Meadows et al., Metabolic and morphological differences between rapidly proliferating cancerous and normal breast epithelial cells. Blotechno! Prog 24, 334-341, (2008).
Medarova et al., In vivo Imaging of siRNA delivery and silencing in tumors. Nat Med 13, 372-377, (2007).
Neeman et al., Metabolic studies of estrogen- and tamoxlfen-treated human breast cancer cells by nuclear magnetic resonance spectroscopy. Cancer Res 49, 589-594, (1989).
Neeman et al., Chemotherapy-induced changes in the energetics of human breast cancer cells; 31 P- and 13C-NMR studies. Biochim Biophys Acta 1052, 256-263, (1990).
Niikura et al., The Role of F-FDG-Positron Emission Tomography/Computed Tomography in Staging Primary Breast Cancer. J Cancer 1, 51-53, (2010).
Padhani et al., Diffusion-weighted magnetic resonance imaging as a cancer blomarker: consensus and recommendations. Neoplasia 11, 102-125, (2009).

(56) References Cited

OTHER PUBLICATIONS

Padhanl et al., Dynamic contrast enhanced MRI of prostate cancer: correlation with morphology and tumour stage, histological grade and PSA. CIO Radio/ 55, 99-109, (2000).
Park et al., Hyperpolarized 13C magnetic resonance metabolic imaging: application to brain tumors, Neuro Onco/ 12, 133-144, (2010).
Phelps et al., Tomographic measurement of local cerebral glucose metabolic rate in humans with (F-18)2-fluoro-2-deoxy-D-glucose: validation of method. Ann Neurol 6, 371-388, (1979).
Pons et al., Breast cancer therapy: the role of PET-CT in decision making. Q J Nuci Med Mot Imaging 53, 210-223, (2009).
Radjenovlc et al., Measurement of pharmacokinetic parameters in histologically graded invasive breast tumours using dynamic contrast-enhanced MRI, Br J Radio! 81, 120-128, (2008).
Reinhardt et al., Quantification of glucose transport and phosphorylation in human skeletal muscle using FDG PET, J Nucl Med 40, 977-985, (1999).
Ross et al., Carbohydrate metabolism of the rat C6 glioma. An in vivo 13C and in vitro 1H magnetic resonance spectroscopy study. NMR Blamed 1, 20-26, (1988).
Ross et al., Clinical experience with 13C MRS in vivo. NMR Biomea '16, 358-369, (2003).
Ross et al., Tumor grade, microvessel density, and activities of malate dehydrogenase, lactate dehydrogenase, and hexokinase in squamous cell carcinoma. *Otolaryngo! Head Neck Surg* 122, 195. 200, (2000).
Rothman et al., 1H{13C} NMR measurements of 4-13C-glutamate turnover in the human brain. *Proc. Nat!. Acad. Sci. USA* 89, 9603-9606, (1992).
Schnell et al., Diagnostic architectural and dynamic features at breast MR Imaging: multicenter study. Radiology 238, 42-53, (2006).
Schouten van der Velden et al., The value of magnetic resonance imaging in diagnosis and size assessment of in situ and small invasive breast carcinoma, Am J Surg 192, 172-178, (2006).
Schupp et al., Localized detection of glioma glycolysis using edited 1H MRS. Magn Reson Med 30, 18-27, (1993).
Schwarz-Dose et al., Monitoring primary systemic therapy of large and locally advanced breast cancer by using sequential positron emission tomography imaging with [18F]fluorodeoxyglucose. J Clin Onco/ 27, 535-541, (2009).
Shapiro et al., In vivo detection of single cells by MRI, Magn Reson Med 55, 242-249, (2006).
Shapiro et al., Dynamic imaging with MRI contrast agents: quantitative considerations. Magnetic resonance imaging 24, 449-462, (2006).
Silva et al., Manganese-enhanced magnetic resonance imaging (MEMRI): methodological and practical considerations. NMR Biomed 17, 532-543, (2004).
Sipkins et al., Detection of tumor anglogenesis in vivo by aiphaVbeta3-targeted magnetic resonance imaging. Nat Med 4, 623-626, (1998).
Sokoloff et al., the [14C]deoxyglucose method for the measurement of local cerebral glucose utilization: theory, procedure, and normal values in the conscious and anesthetized albino rat. J Neurochem 28, 897-916, (1977).
Spence et al., Glucose metabolism in human malignant gliomas measured quantitatively with PET, 1-[C-11)glucose and FDG: analysis of the FDG lumped constant. J Nucl Med 39, 440-448, (1998).
Stephen et al., Promise and progress for functional and molecular imaging of response to targeted therapies. Pharm Res 24, 1172-1185, (2007).
Terpstra et al.,. Lactate turnover in rat glioma measured by in vivo nuclear magnetic resonance spectroscopy. Cancer Res 58, 5083-5088, (1998).
Thie et al., The diagnostic utility of the lognormal behavior of PET standardized uptake values in tumors. JNucl Med 41, 1664-1672, (2000).

Thomsen et al., Nephrogenic systemic fibrosis: A serious late adverse reaction to gadodiamide, Eur Radiol, 16, 2619-2621, (2006).
Tofts et al., Estimating kinetic parameters from dynamic contrast-enhanced T(1)-weighted MRI of a diffusable tracer: standardized quantities and symbols, J Magn Reson Imaging 10, 223-232, (1999).
Toils, P. S. Modeling tracer kinetics in dynamic GD-DTPA MR imaging. J Magn Reson Imaging 7, 91-101, (1997).
Torizuka et al., Untreated primary lung and breast cancers: correlation between F-18 FDG kinetic rate constants and findings of in vitro studies. Radiology 207, 767-774, (1998).
Tseng et al., 18F-FOG kinetics in locally advanced breast cancer; correlation with tumor blood flow and changes in response to neoadjuvant chemotherapy. J Nucl Med 45, 1829-1837, (2004).
Vamesu, S. Angiagenesis and tumor grading in primary breast cancer patients: an analysis of 158 needle core biopsies. Rom J Morphol Embryo) 47, 251-257, (2006).
van Zijl et al., "Use of non-labeled glucose infusion and detection by MRI for assesssing perfusion and metabolism," ICMIC 5P50CA103175-05, pp. 11, 2010.
van Zijl et al., NMR studies of brain 13C-glucose uptake and metabolism: present status. Magnetic resonance imaging 13, 1213-1221, (1995).
van Zijl et al., In vivo proton spectroscopy and spectroscopic imaging of [1-13C]-glucose and its metabolic products. Magn Reson Med 30, 544-551, (1993).
van Zijl et al., MRI detection of glycogen in vivo by using chemical exchange saturation transfer imaging (glycoCEST). Proceedings of the National Academy of Sciences of the United States of America 104, 4359-4364, (2007).
Van Zijl et al., Determination of cerebral glucose transport and metabolic kinetics by dynamic MR spectroscopy. Am J Physic! 273, El 216-1227, (1997).
Vaughan, et al., 71 vs. 4T: RF power, homogeneity, and signal-to-noise comparison in head images. Magn Reson Med 46, 24-30, (2001).
Wahl, Overview of the current status of PET in breast cancer imaging. J Nucl Med 42, 1-7, (1998).
Warburg et al., The Metabolism of Tumors in the Body, J Gen Physic)! 8, 519-530, (1927).
Ward et al., A new class of contrast agents for MRI based on proton chemical exchange dependent saturation transfer (CEST). J Magn Reson 143, 79-87, (2000).
Watanabe et al., DNA synthesis, blood flow, and glucose utilization in experimental rat brain tumors. J Neurosurg 70, 86-91, (1989).
Weidner, N. Tumoural vascularity as a prognostic factor in cancer patients: the evidence continues to grow. J Pathol 184, 119-122, (1998).
Weidner et al., Tumor angiogenesis and metastasis—correlation in Invasive breast carcinoma. N Engi J Med 324, 1-8, (1991).
Weissleder et al., Molecular imaging. *Radiology* 219, 316-333, (2001).
Weissleder et al., Shedding light onto live molecular targets. *Nat Med* 9, 123-128, (2003).
Weissleder et al., Imaging in the era of molecular oncology. *Nature* 452, 580-589, (2008).
Willmann et al., Molecular imaging in drug development. *Nat Rev Drug Discov* 7, 591-607, (2008).
Yankeelov et al., Evidence for shutter-speed variation In CR bolus-tracking studies of human pathology. *NMR Biomecl18*, 173-186, (2005).
Yu et al., In vivo auditory brain mapping in mice with Mn-enhanced MRI. Nat Neurosci 8, 961-968, (2005).
Zelinski et al., Fast slice-selective radio-frequency excitation pulses for mitigating B+1 inhomogeneity in the human brain at 7 Tesla, *Magn Reson Med* 59, 1355-1364, (2008).
Zhou et al., Practical data acquisition method for human brain tumor amide proton transfer (APT) imaging. *Magn Reson Med* 60, 842-849, (2008).

\* cited by examiner glucoCEST $\quad Gl_t(t) = K_1 \int_0^t Gl_p(\tau) e^{-(k2+k3)(t-\tau)} d\tau + v_p Gl_p(t)$ $Gl_t^{SS} = Gl_p^{SS}(v_p + K_1/(k_2+k_3))$ Steady state DCE-MRI $\quad C_t(t) = K^{trans} \int_0^t C_p(\tau) e^{-k_{ep}(t-\tau)} d\tau + v_p C_p(t)$ $K^{trans} = F\rho(1 - e^{-PS/F\rho}) \quad k_{ep} = K^{trans}/v_e$

Fig. 7B

USE OF NON-LABELED SUGARS AND DETECTION BY MRI FOR ASSESSING TISSUE PERFUSION AND METABOLISM

CROSS-REFERENCE OF RELATED APPLICATION

This application is a Divisional of U.S. patent application Ser. No. 13/994,600 filed Jun. 14, 2013, the entire contents of which are hereby incorporated by reference. U.S. patent application Ser. No. 13/994,600 is a national stage application under 35 U.S.C. § 371 of PCT/US2011/064868 filed Dec. 14, 2011, the entire contents of which are incorporated herein by reference. This application claims priority to U.S. Provisional Application No. 61/422,911 filed Dec. 14, 2010, the entire contents of which are hereby incorporated by reference.

This invention was made with Government support under Grant No. 5P50CA103175-05 awarded by the National Institutes of Health. The Government has certain rights in this invention.

BACKGROUND

1. Field of Invention

This patent application relates to methods for magnetic resonance imaging and spectroscopy, and more specifically relates to magnetic resonance (MR) methods for assessing tissue metabolism and perfusion using injection of non-toxic and non-labeled substances

2. Discussion of Related Art

Increased glucose uptake is a well-accepted marker of tumor aggression. In general, tumors tend to have higher glucose utilization and uptake than normal tissue. Following malignancy, glucose uptake in tumors increases dramatically. Glucose uptake, as a biomarker, can be measured by Fluorodeoxyglucose Positron Emission Tomography ($^{18}$FDG-PET), which has become the radiological modality of choice for detecting tumor malignancy. For example, FDG-PET has been proven suitable for detecting and staging primary breast carcinomas and for monitoring response to chemotherapy, as well as many other cancers. However, $^{18}$FDG is a radioactive substance with a half-life of 110 minutes, thus requiring a fresh supply. The use of radioactivity limits repeated frequent use in the same person. In addition PET has low spatial resolution compared to CT and MRI and negligible inherent tissue contrast, leading to the need for anatomical co-registration using CT or MRI.

Other important biomarkers of malignancy include increased permeability of the vascular bed and increased microvessel density, which can be assessed using dynamic contrast-enhanced MRI (DCE-MRI). So far, DCE-MRI has been used to determine tumor grade, extent of disease, and treatment response. For example, recent multi-center results from the International Breast MR Consortium trial concluded that the combined use of architectural (shape) and dynamic contrast features increased specificity for breast MRI. DCE-MRI has been used clinically to image tumor perfusion parameters such as vascular volume and permeability from kinetic modeling of the DCE signal intensity curve as a function of time after bolus injection. However, DCE-MRI relies on the injection of paramagnetic agents such as Gadolinium-DiethyleneTriaminePentaacetic Acid (GdDTPA) that affect relaxation contrast. Such agents have recently been criticized for safety issues in persons with kidney disease (Thomsen, H. S. Nephrogenic systemic fibrosis: A serious late adverse reaction to gadodiamide. Eur Radiol 16, 2619-2621, (2006)).

Thus, there is a need in the art for a methodology to measure abnormalities in tissue metabolism, tissue perfusion and tissue pH that does not use potentially toxic or radioactive exogenous agents and yet is capable of generating sufficient contrast to probe such metabolic and vascular and chemical properties of tissue. This would be especially important for studying tumor malignancy and for monitoring the effects of cancer treatment. If developed, this methodology may reduce false-positive detection rates for cancer by functioning as an add-on for current high-volume screening approaches and to improve treatment monitoring. Another application is for assessing cardiovascular disease, where changes in tissue perfusion parameters and pH may occur during ischemia.

SUMMARY

A method for magnetic resonance (MR) imaging or spectroscopy on a MR scanner to detect tissue physiological parameters in one or more tissue areas in a human or non-human subject according to an embodiment of the current invention includes administering to the subject a contrast enhancing physiologically tolerable amount of a sugar that is non-labeled, subjecting the subject to an MR procedure capable of generating MR signals encoding at least one tissue area in the subject in which the sugar either passes or is taken up, detecting a temporal variation in the MR signals in the at least one tissue area after the administering the sugar, determining at least one tissue-related parameter from the temporal variation, and ascertaining whether the at least one tissue-related parameter is abnormal.

A method for magnetic resonance (MR) imaging or spectroscopy on a MR scanner according to an embodiment of the current invention includes generating a first recorded MR signal by observing a tissue area of a subject under observation in a magnet adapted to provide a characteristic main magnetic field with a corresponding characteristic water proton resonant frequency, generating a second recorded MR signal by repeating the observing at a later time when the subject's blood sugar level is elevated, detecting a difference between the second recorded MR signal and the first recorded MR signal, and subsequently ascertaining a physiological parameter associated with the tissue area of the subject under observation based on the detected difference. A computer-readable medium according to an embodiment of the current invention includes software instructions, which software instructions when executed by a computer, causes the computer, in conjunction with said MR scanner, to implement methods according to embodiments of the current invention.

A toolkit for imaging a subject in a MR system according to an embodiment of the current invention includes an MR-compatible external device constructed to inject a biocompatible dose of sugar in the subject under observation in the MR system, and a sugar analyzer configured to measure blood glucose levels in the subject before, during, and after the dose of glucose is injected into the subject.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
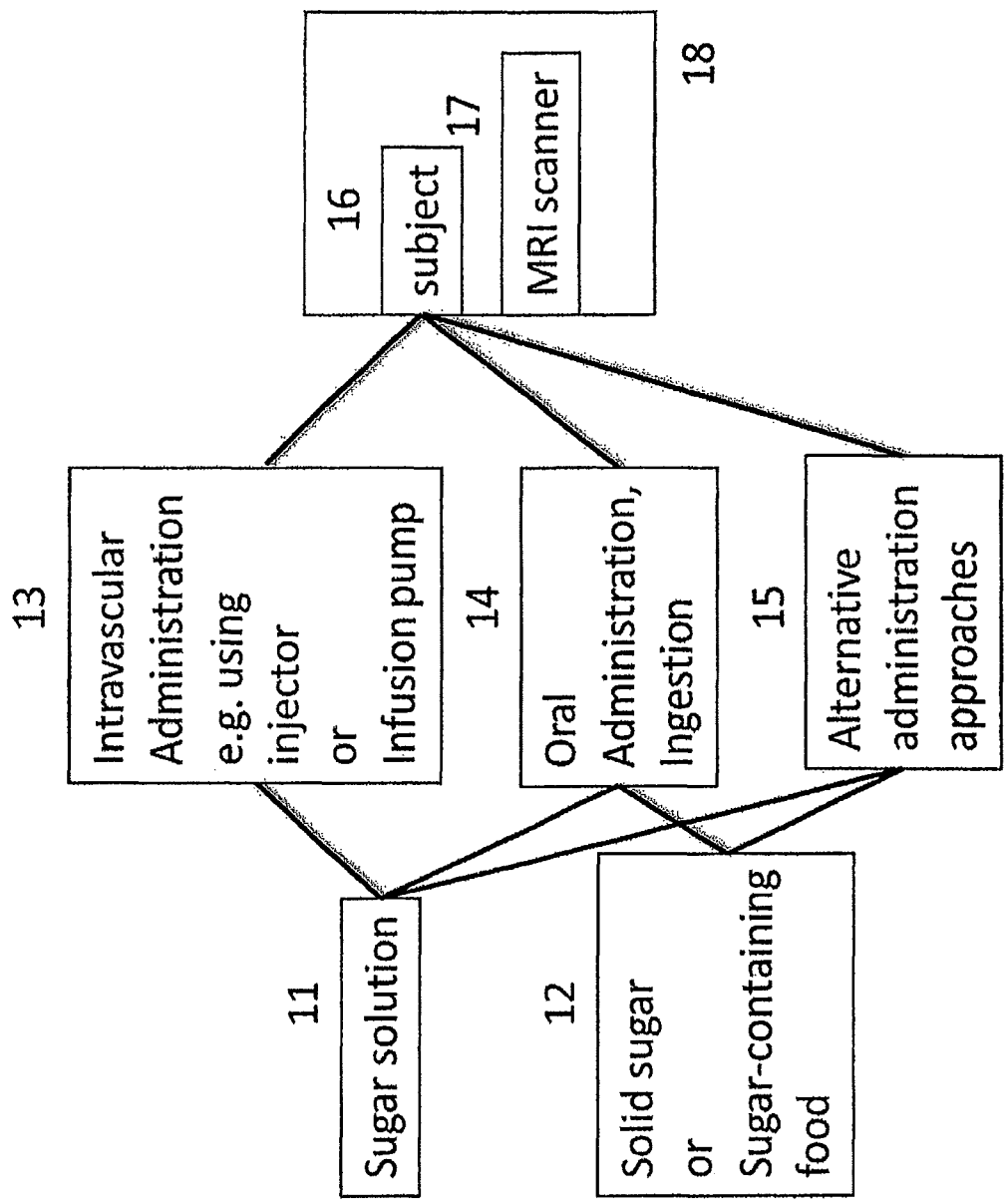
FIG. 1 is a schematic illustration of the procedure of administering the sugar as a contrast agent to the subject, including the monitoring by MRI of the subject, before, during and after administration.

FIG. 1 shows a general scheme of a method according to some embodiments of the invention in which a sugar such as D-glucose or any other suitable biocompatible sugar is administered to a subject in a dose sufficient for changes in MR signals of a subject to be detected. The sugar can be non-labeled according to some embodiments of the current invention. For example, the sugar can be non-radioactive, non-paramagnetic, and not containing non-abundant magnetically enriched isotopes. Such MR signals can be measured before, during and after administration of either a sugar solution (11) or a solid sugar (12) that is either in pure form or in the form of a sugar-containing food. In one embodiment of the invention, administration comprises intravascular administering (13) to the subject of a sugar solution using an injector or infusion pump or any other device for intravascular administration known to those skilled in the field. In another embodiment, the invention employs oral administration and ingestion (14) of a sugar solution or a solid pure sugar or a sugar-containing food. In yet another embodiment, any other method of administration known to those skilled in the field can be used. Administration can be done inside or outside the MRI scanner, but the subject (16) needs to be in the scanner (17) to generate the MR signals that will be used to determine the physiologic parameters. Detection of the administered sugar can employ MR procedures capable of generating signals from the changes in the water resonance due to the presence of the exchangeable protons in said sugar.

Figure 2A:
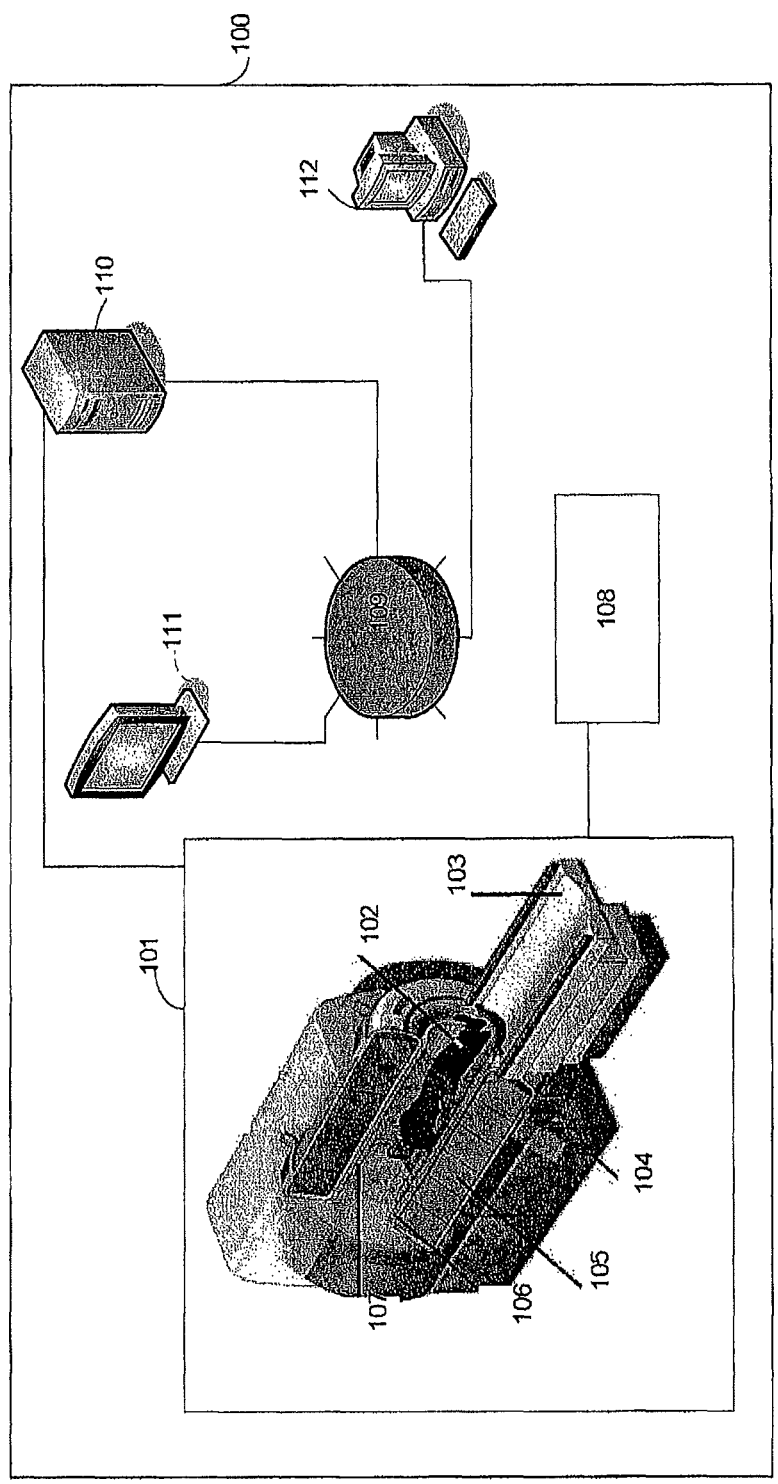
FIG. 2A of a magnetic resonance imaging (MRI) system on which some embodiments of the current invention can be implemented.

FIG. 2A shows an example of a magnetic resonance imaging (MRI) system on which the MRI methodologies according to some embodiments of the current invention can be implemented.

The MRI system 100 includes a magnetic resonance scanner 101, a data storage unit 108, and a signal processing unit 109. Magnetic resonance scanner 101 has a main magnet 105 mounted on base 104 that provides a substantially uniform main magnetic field $B_0$ for a subject 102 under observation on scanner bed 103, a gradient system 106 that provides a perturbation of the main magnetic field $B_0$ to encode spatial information of the constituent water molecules within a region of interest of subject 102 under observation, and a radio-frequency (RF) coil system 107 to transmit electromagnetic waves and to receive magnetic resonance signals from subject 102. MRI system 100 may be a human scanner or and experimental scanner for animals or phantoms containing chemicals.

Subject 102 may be one of an animal, a human, or combinations thereof. Subject 102 is capable of receiving a dose of biocompatible sugar as described in FIG. 1.

The RF coil system 107 may transmit one or more radio frequency (RF) pulses into a tissue area of the subject 102 and monitor a responsive signal induction in order to detect the presence of exchangeable protons. The tissue area, can be, for example, a brain, an esophagus, a breast, a pancreas, a small intestine, a colon, a rectum, a liver, a kidney, a prostate, a uterus, a testicle, a muscle, a joint, etc. The tissue area may be normal or have a physiologic abnormality.

The MR approach used for the detection of the sugar(s) can include any pulse sequences sensitizing the water signal to the presence of the sugar, including but not limited to sequences sensitive to exchange transfer effects in order to detect the presence of exchanging hydroxyl protons. Such exchange-transfer based MR can be done either using a chemical exchange saturation transfer (CEST) pulse sequence or a frequency labeled exchange transfer (FLEX) sequence or similar approaches known to those skilled in the field, or by using changes in relaxation due to the presence of exchangeable protons in the sugar. The CEST or FLEX approaches may include, but are not limited to, the assessment of differences in water signal intensity due to saturation or selective excitation and frequency labeling at different NMR frequencies or ranges of frequencies. Such differences can be expressed, for example, as magnetization transfer asymmetry ratios as known by those skilled in the field.

Such sensitization to exchange can be combined with any possible MRI detection scheme. When performing dynamic imaging to measure changes in sugar concentration as a function of time this will most likely be a fast imaging detection scheme, including, but not limited to, echo planar imaging or fast gradient echo managing. When measuring static or steady state changes in sugar concentration this will most likely employ higher resolution approaches, including but not limited to, FLAIR, MPRAGE and other MRI pulse sequences.

Controller 108 and Data storage unit 109 is in communication with signal processing unit 110 to store the recorded signals. Signal processing unit 110 is in communication with the MR scanner 101. Signal processing unit 110 may be partially or totally incorporated within a structure housing magnetic resonance scanner 101. Signal processing unit 110 may be at least partially incorporated in a workstation that is structurally separate from and in communication with magnetic resonance scanner 101. Signal processing unit 110 may be incorporated in a workstation that is structurally separate from and in communication with magnetic resonance scanner 101.

Signal processing unit 110 may process the recorded signals before and after a dose of sugar is administered to the subject 102 under observation to introduce a change in concentration of exchangeable protons to the tissue area. The processing may comprise analyzing the difference in the recorded signals before and after administration to ascertain a physiologic parameter associated with the tissue area of the subject 102. The physiologic parameter may include, for example, tissue uptake or metabolism or a perfusion parameter (blood flow, blood volume, blood transit time, tissue permeability) or tissue pH.

Figure 2B:
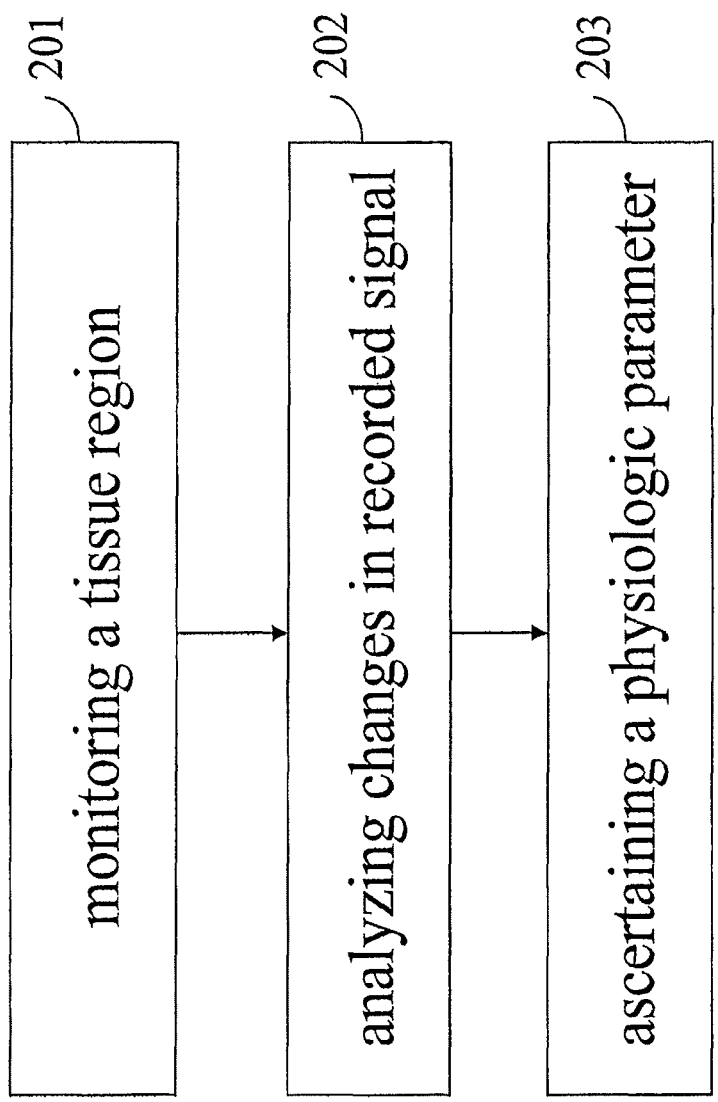
FIG. 2B shows a flow chart of a method as an embodiment of the current invention.

The processed results may be presented to a human observer by an output device in communication with signal processing unit 110. For example, the output device may be a display device, such as, for example, viewing station 111 or a console station 112 or a printer. FIG. 2B shows a flow chart of a method as an embodiment of the current invention. In block 201, a tissue area of a subject 102 is being monitored. The subject 102 may be under observation in the magnet of MR scanner 101 constructed for MR imaging or spectroscopy. The MR scanner can be used to monitor either static (at a certain time point after administration) or dynamic sugar-based water signal changes, by collecting one or more images or spectra while the substance is passing through the body and taken up by it. Such signals can be compared to a reference signal obtained before administration of the sugar or referenced to signals at different time points before, during or after administration. These MR signal changes can then be used to identify regions of normal or abnormal physiologic parameters In block 202 of FIG. 2B, changes in the recorded signals may be analyzed. The changes may result from repeatedly monitoring before and after injecting into the subject 102 a biocompatible dose of sugar that introduces MR-detectable contrast into the tissue area.

In block 203, a physiological parameter associated with said tissue area of said subject may be ascertained. Examples of physiological parameters include but are not limited to the following: tumor perfusion, tissue permeability, tissue perfusion, tissue blood flow, tissue blood volume, tissue mean transit time, tissue sugar uptake, tissue sugar metabolism, etc.

Figures 3A, 3B:
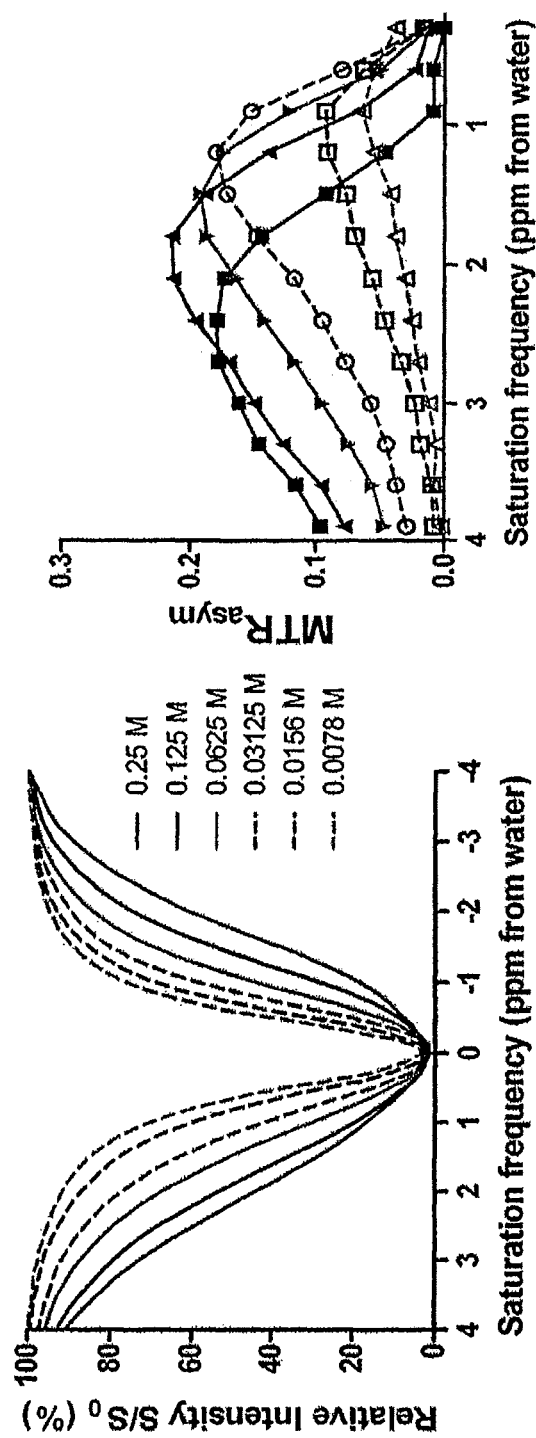
FIGS. 3A and 3B show example measured relative water signal intensity as a function of saturation frequency in a chemical exchange saturation transfer (CEST) MRI experiment and the asymmetry in the magnetization transfer ratio ($MTR_{asym}$) calculated from it, respectively, of a phantom containing varying concentrations of glucose solutions according to some embodiments of the current invention.

FIGS. 3A and 3B show examples of measured relative intensity and asymmetry ratio, respectively, of a phantom containing varying concentrations of glucose solutions according to some embodiments of the current invention. The data were obtained by using a Chemical Exchange Saturation Transfer (CEST) MR sequence, dubbed "glycoCEST" for glycogen and "glucoCEST" for glucose. This sequence is capable of detecting the rapidly exchanging OH groups of glycogen and glucose using CEST in phantoms and in vivo in animals and human. Such detection at first seems implausible due to the limited time available to saturate rapidly exchanging protons, but it can be understood by realizing that for CEST the only requirement is that the life time is sufficiently long to achieve partial saturation. Such partial saturation can be increased by using higher $B_1$ or by reducing the exchange rate.

FIG. 3A illustrates the so-called Z-spectra or CEST spectra for a phantom of D-glucose in PBS buffer (pH=7.3, T=37° C.). In Z-spectra, the relative water signal intensity is displayed as a function of saturation frequency. The profile of such spectra is affected by the presence of exchangeable protons, such as in this case hydroxyl protons. The spectra were acquired using a 9.4 Tesla animal magnet, a B1 field of 3.6 µT and a saturation time of 3.5 seconds. Z-spectra can be analyzed using asymmetry analysis with respect to the water resonance frequency giving a so-called magnetization transfer ratio asymmetry ($MTR_{asym}$) spectrum.

FIG. 3B shows that the shape of the $MTR_{asym}$ spectra varies with glucose concentration. It is important to realize that spectral appearance may also change with power level (higher $B_1$ will broaden the direct saturation line shape in Z-spectra). At the power level used and under the experimental conditions in the sample, the detection sensitivity from FIG. 3B is about 0.5% of water signal per mM D-glucose. In vivo, the plasma concentration is expected to be ramped from baseline (a few mM) up to about 10-20 mM. For tumors, if total plasma and extravascular extracellular space (EES) is 20-40% of the voxel volume, this plasma concentration should give a magnitude of 2-4% in signal change (2.2-4.4M of signal).

Figure 3C:
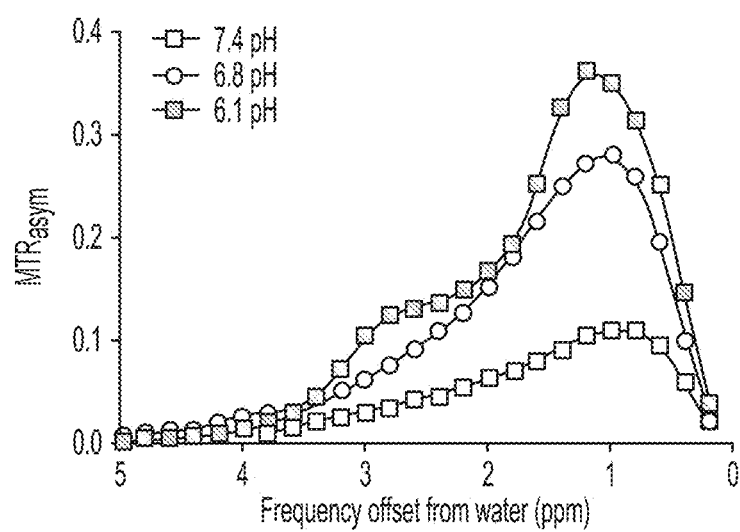
FIG. 3C shows the effect of changes in pH on the glucose-based water CEST $MTR_{asym}$ signal, showing a large increase in exchange transfer effect with reduction of pH.

FIG. 3C shows the appearance of the $MTR_{asym}$ spectrum of glucose as a function of pH. It can be clearly seen that a reduction in pH increases the sensitivity of the OH detection. This is important as it will assist in the detection of cancer if such tumors have an EES in which the pH is low compared to physiological, which is typical for many tumors. In addition, this will allow detection of ischemic tissue, where pH is reduced if anaerobic metabolism is occurring, or any other tissue region with reduced pH.

Tumors are generally characterized by rapid glucose metabolism, increased tissue blood volume, and increased permeability to extravascular extracellular space (EES). We applied glucose infusion in vivo on xenografts in mice for two human breast cancer lines: less aggressive (MCF-7) and highly aggressive and metastatic (MDA-MB-231). Our MRI protocol used normal D-glucose (non-radioactive, non-hyperpolarized and not labeled with magnetic isotopes) and monitored this using glucose-based chemical exchange saturation transfer (glucoCEST) MRI. Images were compared with perfusion as assessed by dynamic contrast-enhanced (DCE) MRI and glucose uptake as assessed by FDG-PET. In-vivo animal experiments employed female SCID mice four to six weeks old. Tumor cells were implanted orthotopically in the mammary fat pad in an aseptic surgical procedure according to Institutional Animal Care and Use Committee (IACUC) guidelines. For cell implantation in the mammary fat pad, mice were anesthetized with ketamine and acepromazine (6.25 mg/kg and 62.5 mg/kg) injected in a volume of 0.05 ml using a sterile insulin syringe (28.5 G needle), and a cell suspension containing $1\times10^6$ MDA-MB-231 cells in 0.05 ml of Hanks balanced salt solution was injected into the upper right thoracic mammary fat pad using a sterile insulin syringe (28.5 G needle). For growth of the estrogen sensitive MCF-7 cells, an estrogen pellet (17β-estradiol, Innovative Research of America, Inc., Cat. No. SE-121) was inserted with a sterilized 10 G trocar needle in the opposite flank at the time of the tumor cell inoculation and the opening will be closed with a single sterile suture clip. The estrogen pellet size, placed at the tip of the trocar, was ~3 mm and the total dose was 0.18 mg/pellet released over 60 days. The procedures were performed in the sterile environment of a laminar flow cabinet. All surgical equipment, including suture clips were sterilized in an autoclave before use. The area of incision and inoculation was swabbed with 70% alcohol and iodine before and after implantation. Following tumor cell implants, animals were monitored until recovered from anesthesia and then checked after 6 and 12 h, then daily.

In vivo MR imaging of the mice was demonstrated at 9.4 T, using a company-supplied transmit and receive coil. Gas anesthesia was delivered using a commercial vaporizer through tubing connected to a nose cone. Animals were kept warm during scanning with the company-supplied heating beds. The lateral tail vein of the anesthetized mouse was cannulated prior to placing the animal on the scanner gantry for injection of glucose or contrast agents. For MR experiments, a home-built catheter was used to minimize dead volume to under 0.04 ml and yet maintain the long lines that are necessary to be able to inject the agents while the animal is in the magnet. The home-built catheter has a PE-60 tubing (0.76 mm inner diameter and 1.22 mm outer diameter, Becton Dickinson) that inserts snugly into a T-connector (1/16", Cole-Parmer, 06365-77). A 4 cm length of PE-60 tubing was inserted into the top arm of the T-connector, and a 25 G⅝ needle cleared of its base fits snugly into the other end of the 4 cm PE-60 piece to insert in the tail vein. The remaining two arms of the T-connector were used to attach a PE-60 tube connected to a 3 ml syringe with 0.5 M glucose solution positioned in an infusion pump (as described below) and the other arm of the T-connector was hooked to a line containing the contrast agent that can be opened or closed with a one-way stop-cock. An additional line containing saline was used to test the potency of the tail vein.

For glucose infusion, sterile glucose solution in water (0.5 M or 90 g/L) was infused to the tail vein. An initial loading bolus of 0.1 ml was followed by the continuous infusion with exponentially decreasing rates from 0.5 ml/h to 0.05 ml/h to maintain the target blood glucose concentration of 20 mM.

FIG. 4 shows preliminary glucose delivery and uptake data in a mouse inoculated with MDA-MB-231 (2.5 weeks) and MCF-7 (1 month) xenografts, with the growth period based on approximate volume matching (the malignant MDA-MB-231 grows faster). The mouse was infused with 0.5 M D-glucose in saline via the tail vein using an initial loading bolus followed by a maintenance infusion at decreasing infusion rates that provide stable steady-state blood glucose concentrations at about 20 mM (about 4-5 times the normal blood concentration). GlucoCEST MRI was performed during steady state before infusion (40-min scan) and after blood glucose stabilization (40 min scan). The GlucoCEST sequence used had a Rapid Acquisition Rapid Echo (RARE) readout, a slice thickness of 1.5 mm, an in-plane resolution of 0.4 mm×0.5 mm, Z-spectra based on 29 saturation frequencies and a total acquisition time of 40 minutes. Thereafter, a DCE-MRI with 0.2 mmole/kg GdDTPA was performed.

Figure 4A:
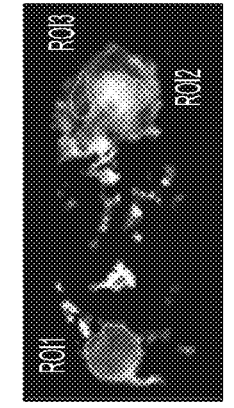
FIG. 4A shows a Magnetization Transfer Ratio (MTR) asymmetry image at offset 1.2 parts-per million (ppm) for a mouse inoculated with two tumor xenografts before glucose infusion.

FIG. 4A shows a MTR asymmetry image at offset 1.2 ppm from the proton water resonance frequency for a mouse inoculated with xenograft tumor before glucose infusion.

Figure 4B:
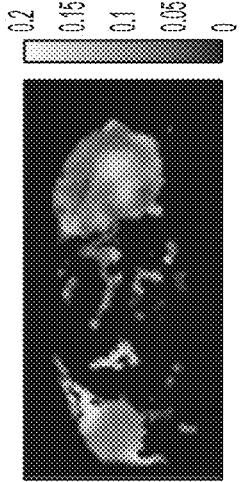
FIG. 4B shows a MTR asymmetry image at offset 1.2 ppm for a mouse inoculated with xenograft tumor after glucose infusion.

FIG. 4B shows a MTR asymmetry image at offset 1.2 ppm for a mouse inoculated with xenograft tumor after glucose infusion.

Figure 4C:
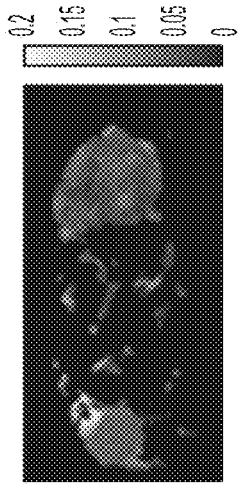
FIG. 4C shows the difference image between FIGS. 4a and 4b.

FIG. 4C shows the difference image between FIGS. 4A and 4B. Three regions of interest (ROIs), namely, ROI 1 through ROI 3, are identified on the difference image.

Figure 4D:
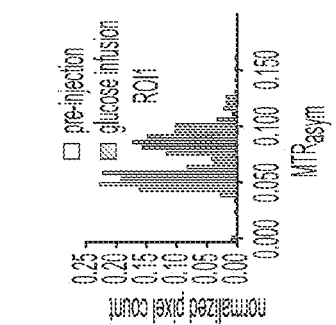
FIG. 4D shows the respective Z-spectra (relative water signal intensity as a function of saturation frequency) before and after infusion.

FIG. 4D shows the respective Z-spectra before and after infusion.

Figure 4E:
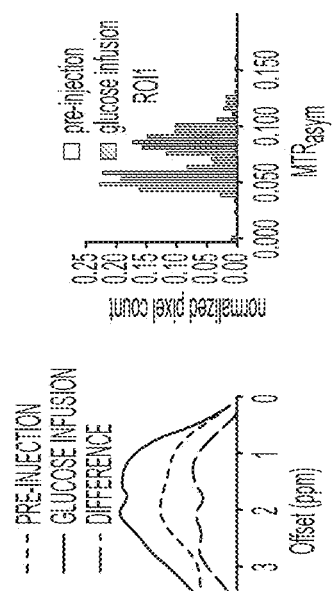
FIG. 4E shows the respective MTR asymmetry ratios before and after infusion.

FIG. 4E shows the respective MTR asymmetry ratio before and after infusion as well as the difference between them.

Figure 4F:
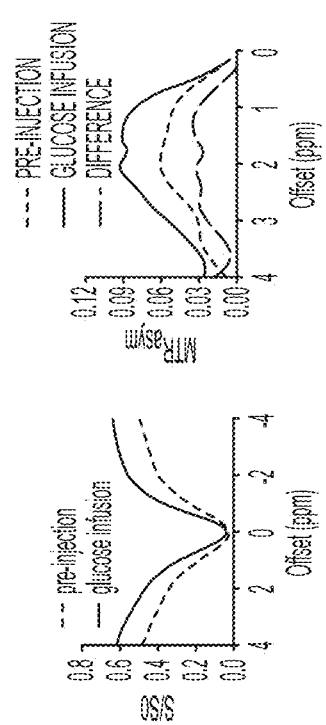
FIG. 4F shows the respective MTR asymmetry histograms before and after infusion for a first region of interest.
Figure 4G:
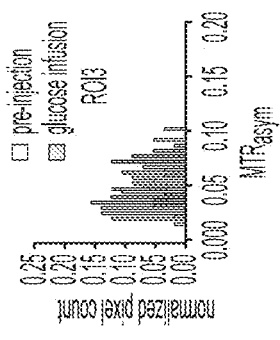
FIG. 4G shows the respective MTR asymmetry histograms before and after infusion for a second region of interest.
Figure 4H:
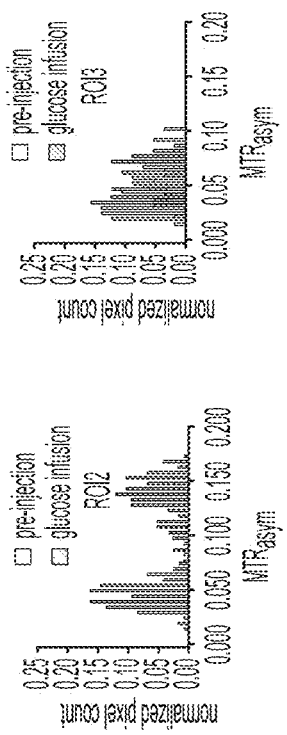
FIG. 4H shows the respective MTR asymmetry histograms before and after infusion for a third region of interest.

FIG. 4F shows the respective MTR asymmetry histograms before and after infusion for three different regions of interest, showing a trend towards higher glucose uptake in the malignant MDA-MB-231 tumor (ROI 1) as well as in the necrotic area in the MCF7 tumor (ROI 2). These promising preliminary data further demonstrate the feasibility of using non-labeled glucose to probe tumor metabolism and perfusion parameters.

Figure 5A:
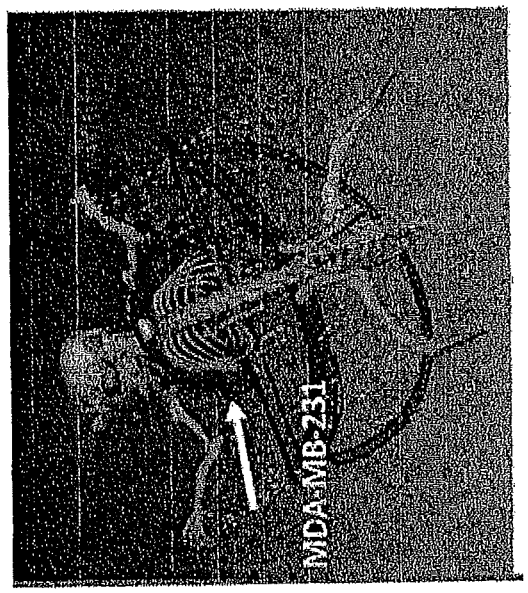
FIG. 5A shows an reconstructed CT image of the mouse skeleton with the locations of the two tumor xenographts (MDA-MB-231 and MCF7) indicated.
Figure 5C:
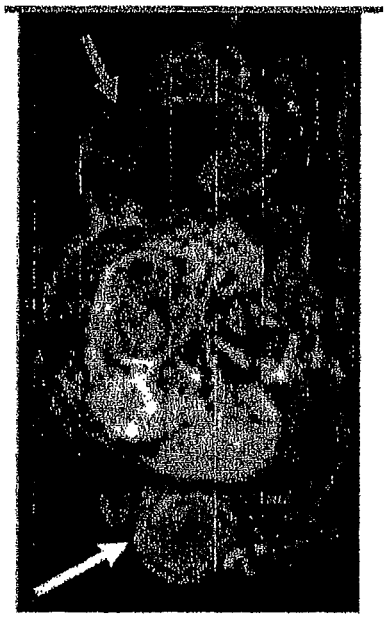
FIGS. 5B and 5C show representative $^{18}$F-FDG-PET and post-Gd-DTPA difference images for this mouse.
Figure 5B:
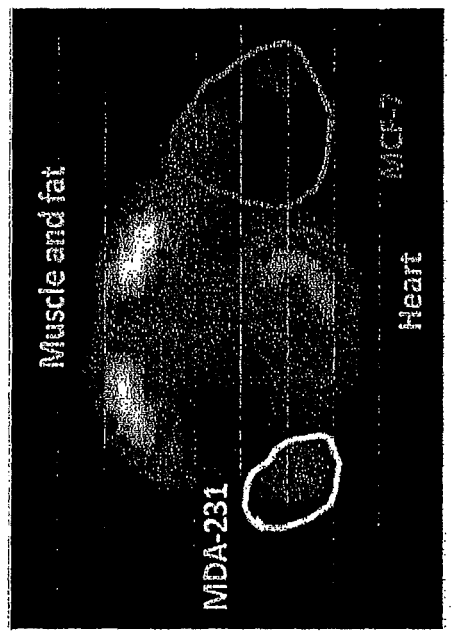

FIG. 5A shows a reconstructed CT image of the mouse skeleton with the locations of the MDA-MB-231 tumor and the MCF7 tumor indicated. FIGS. 5B and 5C show representative $^{18}$F-FDG-PET images and post-Gd-DTPA difference images for this mouse, respectively. In FIG. 5B, the MDA-MB-231 tumor exhibits a higher glucose uptake than the MCF-7 tumor on PET at 1 hr post-injection, in line with literature. In FIG. 5C, the Gd-DTPA data demonstrates good visualization of the tumor mass relative to normal tissue. Interestingly, the Gd perfusion scan did not highlight the necrotic area in the MCF7 tumor, while the glucose infusion did. This may be due to the different plasma kinetics and indicate different transport properties for the Gd agent versus D-glucose, which will be further investigated. The Gd acquisition for this mouse did not allow quantitative analysis. Glucose uptake and metabolism are well-known to be increased in malignant tumors, a phenomenon exploited in FDG PET. Also, tumor vascularity is generally increased through angiogenesis. Thus, the preliminary data suggest that infusion of non-labeled D-glucose and detection with CEST MRI can provide combined information about glucose uptake and perfusion.

Even though the procedure of looking at steady state glucose uptake at a certain time point post infusion should already provide a viable technique (similar to clinical PET where data are taken at a single time point post-infusion), it is also possible to speed up these experiments so that one can measure active uptake and perform quantitative analysis of combined glucose delivery and utilization rate. In fact, speeding up CEST may not be difficult as in principle less irradiation frequencies, e.g. measure only differences at a single frequency of the broad glucose saturation spectrum (e.g., around 1.2 ppm) may be used during infusion. This reduction may avoid the need for CEST asymmetry analysis by measuring only difference signals. As the glucose resonance is quite broad, a small miss-setting of the frequency due to local differences in field inhomogeneity should not be a problem. In addition, before measuring the kinetics, the exact water frequency can be quickly measured using field mapping procedures available on MRI scanners, including but not limited to our water saturation shift reference (WASSR) scheme that uses the same MR scheme as CEST and water frequencies.

Figure 6A:
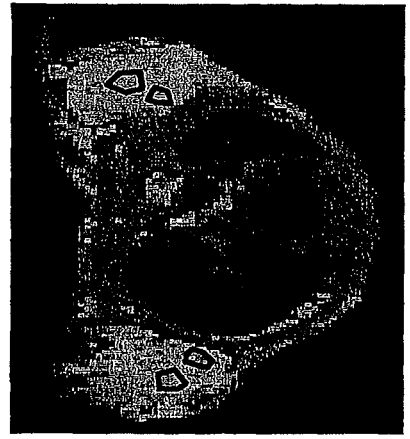
FIG. 6A shows the MTR asymmetry images as a function of time during D-glucose infusion for the two implanted xenografts during the infusion.
Figure 6B:
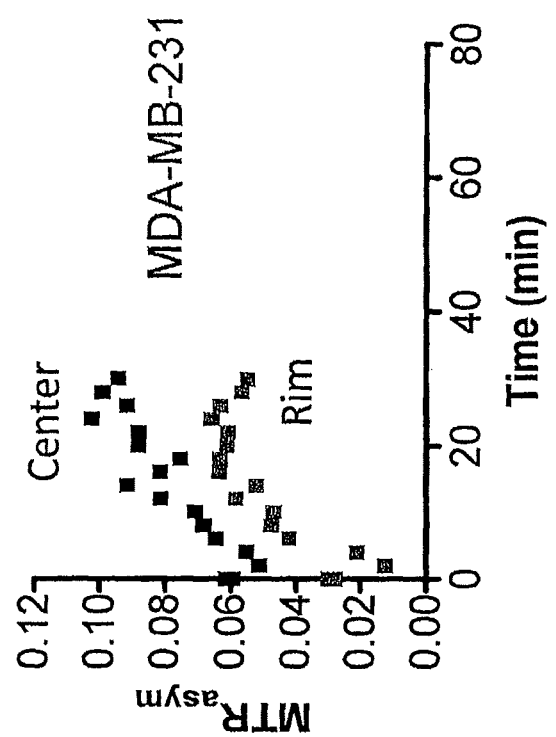
FIG. 6B shows the $MTR_{asym}$ signal changes as a function of time during D-glucose infusion for the MDA-MB-231 xenograft in the rim and tumor center
Figure 6C:
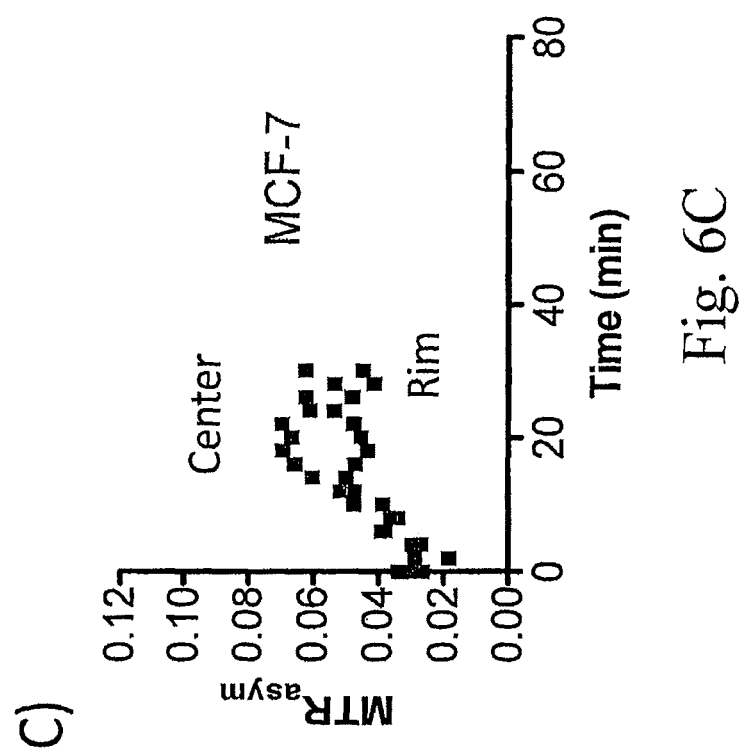
FIG. 6C shows the $MTR_{asym}$ signal changes for the MCF7 xenograft in the rim and tumor center FIG. 7A compares the parameter definitions for kinetic analysis of the MR-CEST glucose method with those of PET 11C-glucose, PET 18FDG glucose and dynamic contrast enhanced MRI.

FIGS. 6A-6C show results for a D-glucose infusion experiment with dynamic monitoring of the MR exchange transfer signals for a mouse with two tumor xenografts (MDA-MB-231 and MCF7) at 11.7 T for which a D-glucose infusion protocol similar to the example in FIG. 4 was used. FIG. 6A shows the MTR asymmetry images for the two implanted xenografts at the time point of maximal signal change. FIG. 6B shows the $MTR_{asym}$ signal changes as a function of time during infusion for the MDA-MB-231 xenograft in the rim and tumor center. FIG. 6C shows the $MTR_{asym}$ signal changes as a function of time during infusion for the MCF7 xenograft in the rim and tumor center. It can be seen that the uptake is higher in the more malignant MDA-MB-231 tumor.

Figure 7A:
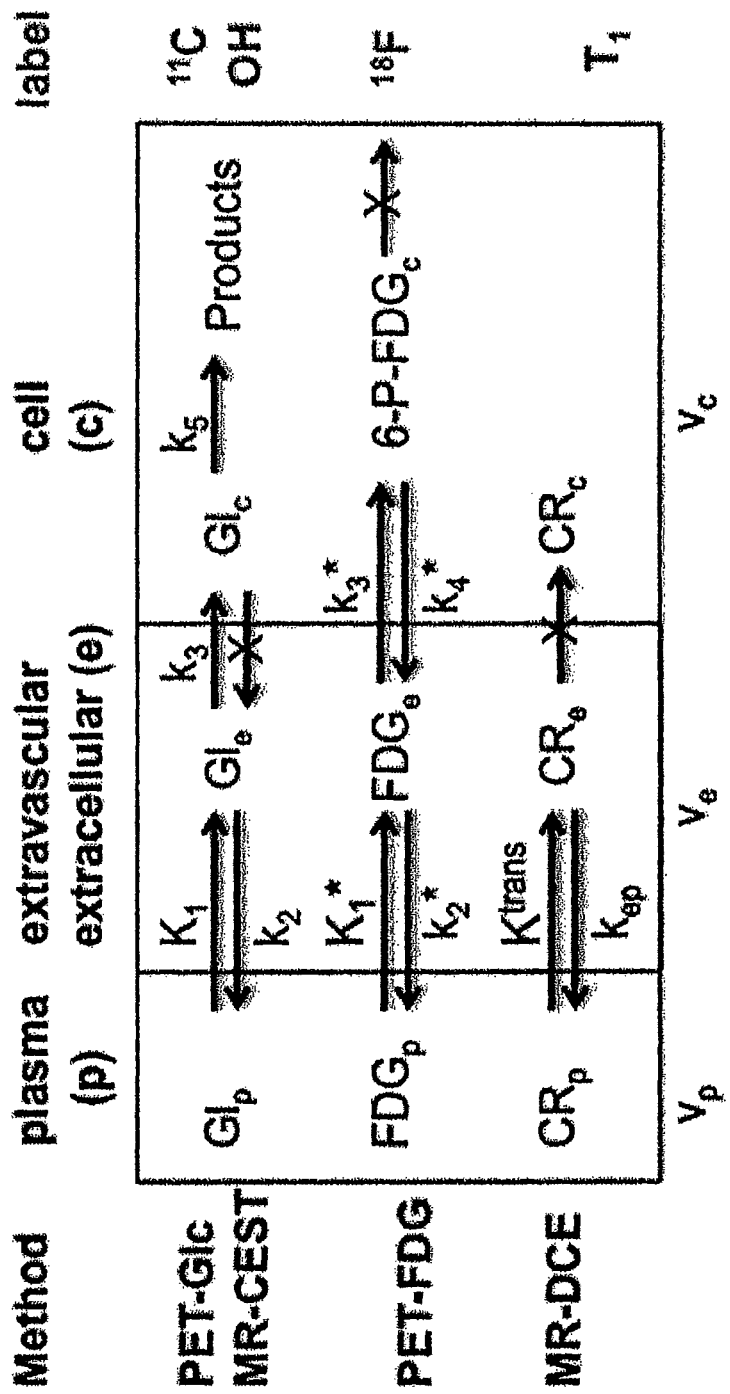
FIG. 7B compares the working equations for the quantitative analysis of glucoCEST data during glucose perfusion, uptake and metabolism with those for the DCE-MRI method.

FIG. 7A compares the parameter definition for kinetic analysis for glucose uptake in tumors, for 11C-glucose PET (PET-Glc), glucoCEST (MR-CEST), FDG-PET (PET-FDG) and DCE-MRI. The envisioned kinetic analysis includes uptake, efflux, tissue permeability, and metabolism. PET-FDG constants are denoted with an asterisk as FDG uptake and metabolism differs from glucose, which is usually accounted for through a lumped constant. Capital K indicates the transfer constant into the extravascular extracellular space and small k rate constant, but the units of K1 (ml/g/min) and Ktrans (min-1) differ by the multiplication with density (g/ml) for Ktrans. Abbreviation are illustrated as: Gl=glucose; CR=contrast reagent, b=blood; v=volume fraction; t=total; V=volume; Vt=Vb+Ve+Vc; Hct=hematocrit; Vp=Vb(1−Hct); n=volume fraction=Vi/Vt; i=p,e,c.

The active equations for glucoCEST (MR-CEST), $^{11}$C-PET FDG-PET and DCE-MRI are very similar and are summarized for glucoCEST and DCE-MRI in FIG. 7B. To date, no universal strategy for analysis of DCE-MRI has been formulated and most groups use simple two-compartment kinetic models as indicated in FIGS. 7A and B that can provide the fractional volume of EES ($v_e$), the rate constant for reflux of GdDTPA from EES back to plasma ($k_{ep}$), and the transfer constant characterizing extravasation of GdDTPA from plasma ($K^{trans}$). This two-compartment model has shown potential for breast tumor grading, allowing detection of statistically significant differences between various grades of tumor. DCE-MRI relies on $T_1$ contrast, but one of the assumptions, fast exchange of water between compartments is not really valid in the most commonly used clinical pulse sequence approaches, which affects the parameter values. Accounting for this so-called shutter-speed effect allowed improved separation of the vascular properties of benign and malignant tumors. The glucoCEST equations were derived in analogy to $^{11}$C-glucose and $^{13}$C-glucose, assuming typical tumor microenvironment conditions: (i) negligible backflow of glucose from cell to interstitium (i.e., $k_4$~0) and (ii) instantaneous disappearance of glucoCEST signal upon cell entry due to rapid phosphorylation and glycolytic conversion, as supported by extremely low cellular equilibrium concentrations of the glycolytic intermediates glucose-6-phosphate (~80 µM), fructose-6-phosphate (~14 µM), and fructose-1,6-bisphosphate (~30 µM) that can contribute to glucoCEST via OH groups. To establish the input function, $Gl_p(t)$, time-dependent blood glucose concentrations may be measured with a standard glucose analyzer (radiometer) in a separate group of tumor bearing animals outside the scanner.

The method described relates to administering a sufficient amount of sugar, that accomplishes either an MR detectable blood sugar concentration change or the buildup in tissue of an MR detectable amount of the sugar. The detectable range of sugar depends on the magnetic field used (smaller concentrations can be detected at the more sensitive higher fields for MRI, the radiofrequency coil used and the subject's perfusion and metabolic parameters, and the pH of the tissue. The following general guidelines apply for sugars with protons of normal MR polarization (i.e. not hyperpolarized). The detectable amount corresponds to the MR effect of the concentration of exchangeable protons when using a sugar with one hydroxyl group at a blood or tissue concentration in the range of about 50 µM or more at normal tissue pH. Lower concentrations can be detected when increasing the number of hydroxyl groups in a sugar, increasing the concentration of the sugar in the administered volume of an intravascular bolus or infusion, or increasing the volume of the administration of the intravascular bolus or infusion of the sugar, or increasing the amount of solid sugar or sugar containing food in the case of oral administration. Other ways to lower this concentration would be either by changing the pH of the infusate to enhance detectability of the sugar, monitoring tissues that have a pH that enhances detectability of the sugar, including but not limited to the extravascular extracellular space of tumors, enhancing the exchange rate of the hydroxyl group through synthetic modification of the sugar, enhancing the polarization of other protons in the sugar and transferring that to the hydroxyl protons, enhancing the polarization of other nuclei in the sugar and transferring said polarization to the hydroxyl protons in the sugar either directly or via the protons in the sugar.

The dynamic analysis may provide an alternative for dynamic and static perfusion imaging with Gd-DTPA and other paramagnetic contrast agents, which can then be used to assess for instance, tumor perfusion, blood brain barrier permeability, tissue perfusion, tissue blood flow, tissue blood volume, tissue mean transit time. In addition, glucose kinetics can relate to both perfusion and tissue metabolism. Thus the use of non-labeled glucose infusion and measurement by MRI may provide an alternative to current methods using radioactive substances, such as FDG-PET, to probe metabolism.

For PET, by contrast, values for $K_1$, $k_2$, and $k_3$ can in principle be derived using the Sokoloff 3-compartment model. To date, only few publications on clinical PET-FDG of breast cancer employ quantitative kinetics. The majority of studies measure the dimensionless standardized uptake value (SUV=organ uptake (Bq/g)×bodyweight (g)/injected dose (Bq)), which is proportional to $K_1k_3/(k_2+k_3)$ and can provide a semi-quantitative measure of accumulation by normalizing organ tissue radioactivity at 60 min post-injection to the injected dose and body weight. The most comprehensive study on breast cancer known to the authors was on SUV in 46 benign and 51 malignant tumors, showing more than double the SUV in malignancy. We foresee that the non-labeled glucose experiment proposed here will also allow the determination of a specific uptake value for glucose in tumors, but then based on D-glucose.

The methodology, discussed above according to some embodiments of the current invention, may be used for tumor detection, imaging tumor perfusion and metabolism, assessing tumor malignancy, and monitoring tumor treatment. Such methodology may reduce false-positive detection rates by functioning as an add-on for current high-volume screening approaches and to improve treatment monitoring.

To the extent that $B_0$ variation across the sample can lead to systematic errors in the CEST asymmetry analysis for the steady state method, a WAter Saturation Shift Referencing (WASSR) method may be used to correct for this. For kinetics experiments in which signal differences at one frequency will be measured, as explained above, susceptibility to $B_0$ variation will be less pronounced. A time resolution on the order of seconds (similar to fMRI and DCE-MRI) is expected. Imaging speed also depends on the spatial resolution used and can be increased using parallel imaging and EPI methods. Because ultimately the methodology according to some embodiments of the current invention is a water detection method, all commonly available fast imaging methods that remain within specific absorption ration (SAR) guidelines when combined with sugar-sensitive pulse sequences including saturation or other exchange transfer approaches can be used.

Thus, some embodiments of the current invention provide a methodology of MRI monitoring of non-labeled glucose infusion. In particular, the methodology can measure MR contrast sensitive to both metabolic and vascular properties (perfusion and permeability) of tissue. In addition, the methodology uses a biocompatible compounds (sugars, including but not limited to D-glucose). Finally, in contrast to current magnetically labeled isotopes (e.g. $^{13}$C-labeled) approaches, the method according to some embodiments of the current invention uses water imaging for detection. Thus, the method according to some embodiments of the current invention is directly compatible with clinical scanners.

Figure 8:
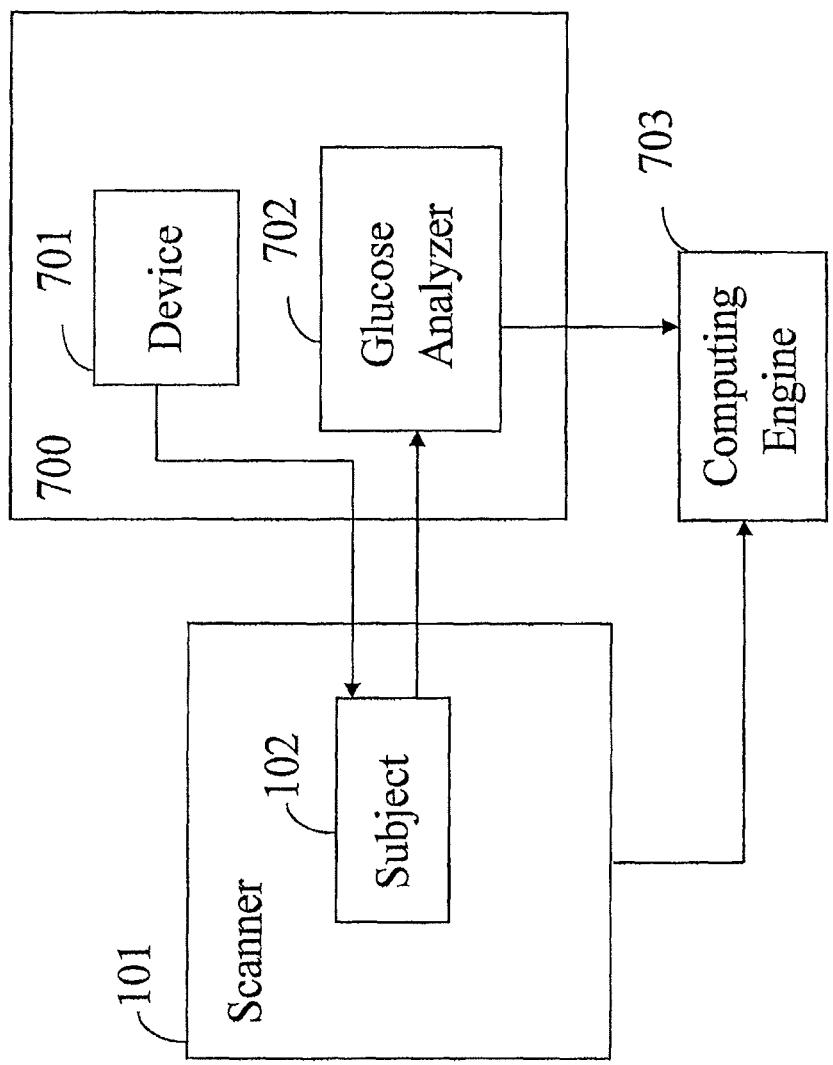
FIG. 8 is a schematic illustration of a toolkit for imaging a subject in a MR system according to an embodiment of the current invention.

Some embodiments of the current invention may provide a toolkit for imaging a subject in a MR system, as shown in FIG. 8. The toolkit 700 may comprise at least one of: a MR-compatible device 701 constructed to inject a biocompatible dose of glucose sufficient to generate MR contrast in the subject under observation in the MR system, a MR-compatible glucose analyzer 702 configured to measure blood glucose level in the subject before, during, and after the dose of glucose is injected into the subject. MR compatible means capable of being operative inside a magnet for MR scanning 101 or inside an MR scanner room or outside an MR scan room, but connected to the subject in the MR scanner. For example, ferromagnetic materials are not MR-compatible. The device 701 may comprise one of: an external device or an intravascular applicator. An external device may comprise, for example, an infusion pump capable of being synchronized with data acquisition on the MR system.

The toolkit 700 may further comprise a computing engine 703, in communication with the MR system and the glucose analyzer 702. The computing engine may be programmed to: receive at least one of: measured data from the MR system or measured glucose level from the glucose analyzer 702, the measured data comprising MR signal changes due to injection of the dose of glucose into the subject; and compute a physiologic parameter based on at least one of: the measured data or the measured glucose level, the physiologic parameter comprising: a perfusion parameter or a metabolism parameter; and output the physiologic parameter to a user. It may also be possible to determine a sugar input function based on specific time dependent MR data and not use the glucose analyzer, and to use this MR-determined input function for calculating physiologic parameters.

The physiologic parameter may be computed based on one of: an empirical model, or an analytic model. An empirical model is not based on an analytic model and may include, for example, an area under the curve, etc. An analytic model may include, for example, the compartmental modeling as discussed above. The physiologic parameter may comprise one of: a standard uptake value, a permeability parameter, a tissue mean transit time, or a tissue blood volume, or other related physiologic parameters as specified above.

Computing engine 703 may be a computer with at least one central processing unit (CPU) and a plurality of memories. Computing engine 703 may also be a dedicated processing machine with such devices as, for example, a field programmable gated array (FPGA), a digital signal processing (DSP) chip, a graphic processing unit (GPU), an application specific integrated circuit (ASIC), etc. Computing engine 703 may also be incorporated in the MR scanner 101.

An embodiment of the invention provides a toolkit that includes a prepared sugar solution or sugar-containing solid or liquid food in a prescribed concentration (most likely ranging from, but not limited to, 1% weight fraction to 100% weight fraction) and in the appropriate amount for MR detection such that the sugar is in ampules or solid form and can be used immediately either with an available MR-compatible injector or infusion pump or as oral contrast agent.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for magnetic resonance (MR) imaging or spectroscopy on a MR scanner, comprising:
generating a first recorded MR signal by observing at a first time a tissue area of a subject with a pulse sequence implemented on the MR scanner, said pulse sequence adapted to sensitize said first recorded MR signal to the presence of sugar in said tissue area;
administering sugar to said subject to cause said subject's blood sugar level to become elevated; and
generating a second recorded MR signal by repeating said observing of said tissue area of said subject with said pulse sequence at a second, later time when the subject's blood sugar level is elevated;
detecting a difference between the second recorded MR signal that is sensitized to an elevated level of sugar in said tissue area at the second, later time and the first recorded MR signal that is sensitized to a baseline level of sugar in said tissue area at the first time;
subsequently ascertaining at least one physiological parameter associated with perfusion of blood in said tissue area of said subject under observation based on the detected difference; and generating a plurality of recorded MR signals prior to, during, and after said administering said sugar to said subject, wherein said MR scanner is adapted for measuring changes in water MR signals based on a changed water relaxation rate caused by said administered sugar comprising one or more hydroxyl protons that are exchangeable with water molecules in said tissue.

2. A method according to claim 1, wherein said generating said first recorded MR signal is performed prior to said administering and said generating said second recorded MR signal is performed during said administering.

3. A method according to claim 1, wherein said generating said first recorded MR signal is performed during said administering and said generating said second recorded MR signal is performed after said administering has been stopped.

4. A method according to claim 1, wherein said at least one physiologic parameter is one of a sugar uptake, a sugar metabolism or pass-through speed, a perfusion parameter, a blood volume, a pH, and a permeability parameter.

5. A method according to claim 1, wherein said MR scanner is adapted to provide a selective saturation or a frequency labeling of exchangeable hydroxyl protons of at least one sugar molecule.

* * * * *